United States Patent [19]

Miyata et al.

[11] 4,134,880

[45] Jan. 16, 1979

[54] PROCESS FOR PRODUCING AN AROMATIC URETHANE FROM NITRO COMPOUNDS, HYDROXYL COMPOUNDS AND CARBON MONOXIDE USING METAL-LEWIS ACID-AMMONIA CATALYST SYSTEMS

[75] Inventors: Katsuharu Miyata; Yutaka Hirai; Hiroshi Yoshida, all of Omuta, Japan

[73] Assignee: Mitsui Toatsu Chemicals, Incorporated, Tokyo, Japan

[21] Appl. No.: 870,890

[22] Filed: Jan. 19, 1978

[51] Int. Cl.² .............................................. C08L 79/00
[52] U.S. Cl. ............................... 560/24; 260/29.2 TN; 560/24; 560/25; 560/26; 560/32; 528/422; 528/211
[58] Field of Search .......... 260/47 CP, 2 R, 29.2 TN; 560/24, 25, 26, 32

[56] References Cited

U.S. PATENT DOCUMENTS

| | | | |
|---|---|---|---|
| 3,338,956 | 8/1967 | Mountfield | 560/24 |
| 3,448,140 | 6/1969 | Gamlen et al. | 560/24 |
| 3,454,620 | 7/1969 | Gamlen et al. | 560/32 |
| 3,467,694 | 9/1969 | Hardy et al. | 560/24 |
| 3,531,512 | 9/1970 | Hardy et al. | 560/25 |
| 3,993,685 | 11/1976 | Zajacek et al. | 560/24 |
| 4,052,420 | 10/1977 | Licke | 560/25 |
| 4,052,437 | 10/1977 | Licke | 560/24 |

Primary Examiner—M. J. Welsh
Attorney, Agent, or Firm—Fisher, Christen and Sabol

[57] ABSTRACT

An aromatic urethane of high quality and excellent heat stability can be produced in high yield by reacting an aromatic nitro compound, a hydroxyl group-containing organic compound and carbon monoxide in the presence of a catalytic system composed of (1) palladium, ruthenium, rhodium or a compound thereof, (2) a Lewis acid, and (3) ammonia. The use of such catalytic system can suppress undesirable side reactions to a satisfactory extent and ensures the reaction to proceed without causing any corrosion of a stainless steel reactor. If necessary, water may be added to the reaction system to increase the reaction velocity, by which the unit cost of the catalyst can be reduced.

8 Claims, No Drawings

PROCESS FOR PRODUCING AN AROMATIC URETHANE FROM NITRO COMPOUNDS, HYDROXYL COMPOUNDS AND CARBON MONOXIDE USING METAL-LEWIS ACID-AMMONIA CATALYST SYSTEMS

BACKGROUND OF THE INVENTION

1. Field of the Invention

This invention relates to a process for producing aromatic urethanes. More particularly, it relates to a process for producing aromatic urethanes by reacting aromatic nitro compounds, organic compounds containing at least one hydroxyl group (hereinlater referred to as hydroxyl group-containing organic compound) and carbon monoxide under high temperature and high pressure conditions in the presence of a catalyst of a specific type.

2. Description of the Prior Art

As well known, urethanes have been heretofore produced mainly by reaction of isocyanates and hydroxyl group-containing organic compounds. In recent years, several novel processes for producing urethanes have been proposed because of the lack and high cost of starting materials for producing the isocyanates and also high toxicity of the intermediates derived from the starting materials. However, such newly developed processes have several vital drawbacks and have not been yet put into practice on an industrial scale.

For instance, there has been proposed a process in which an aromatic urethane is produced from an alcohol, carbon monoxide and an aromatic nitro compound by use of a rhodium chlorocarbonyl catalyst (U.S. Pat. No. 3,338,956). However, this process is not economically advantageous in producing highly pure aromatic urethanes since the yield of the urethane product is low even if the reaction is effected in the presence of a large amount of a catalyst for a long period of time.

In order to improve the above process, there has been also proposed another process using a compound containing a carbonyl group of a metal of the group VIII of the Period Table and a metal salt capable of existing in a state of a di- or higher valence such as ferric chloride (German Pat. No. 1,543,051). However, this process is not practical since the yield of a urethane product is still low even when a mononitro compound is used as a starting material and use of a dinitro compound will result in lower yield.

There is also known a process using palladium and a Lewis acid as a catalyst (U.S. Pat. No. 3,531,512). According to the process, even when a dinitro compound is employed as a starting material, the yield of urethane as high as 80–90% may be attained. In order to attain such high yield, however, the reaction must be conducted under severe conditions such as of an initial pressure of carbon monoxide of 190–350 kg/cm$^2$ and a reaction temperature of 190–200° C. In addition, the process involves an industrially serious problem that a Lewis acid, e.g., ferric chloride, serving effectively as a promoter exerts a considerable corrosive action on a metal material such as iron, stainless steel, or the like. In order to realize the process on an industrial scale, it is accordingly essential to use a glass or tantalum reactor, offering serious economical and technical problems.

There is known a further process using a catalyst composed of a platinum group metal compound and a tertiary amine (U.S. Pat. No. 3,993,685). However, this process needs a large amount of the catalyst and is thus uneconomical.

Quite recently, there has been proposed a process in which a ternary catalytic system composed of a member selected from palladium, ruthenium, rhodium and a compound thereof, a Lewis acid, and a tertiary amine is used and the reaction is conducted in coexistence with water, if desired (Japanese Patent Application No. 69721/'76). However, even this process can hardly produce aromatic urethanes of high quality and excellent heat stability.

SUMMARY OF THE INVENTION

It is an object of the present invention to provide a process for producing aromatic urethanes in high yield which are thermally more stable and higher in quality than those obtained by prior art processes.

It is another object of the present invention to provide a process using a catalytic system which is easy to prepare and handle, low in toxicity and easy in recovery.

According to the present invention, there is provided a process for producing aromatic urethanes of high quality in high yield, the process comprising reacting an aromatic nitro compound, a hydroxyl group-containing organic compound selected from the group consisting of monohydric alcohols, polyhydric alcohols, monohydric phenols and polyhydric phenols, and carbon monoxide in the presence of a catalytic system composed of (1) a member selected from elemental palladium, ruthenium and rhodium, and their halides, cyanides, thiocyanides, isocyanides, oxides, sulfates, nitrates and carbonyl compounds, (2) a Lewis acid, and (3) ammonia under an initial pressure of carbon monoxide of 10–500 kg/cm$^2$ at a temperature of 80–260° C. After completion of the reaction, most of the catalyst is removed from the reaction solution by filtration. The crude aromatic urethane obtained by drying up the resulting filtrate does not contain any appreciable amounts of catalytic components such as, for example, $FeCl_2$, $NH_3$, $PdCl_2$, etc., so that the crude aromatic urethane can be immediately thermally decomposed into a corresponding isocyanate. In this instance, when, for example, crude 2,4-dinitrotoluene is produced by use of a known catalytic system composed of palladium, a Lewis acid and a tertiary amine, the purity of the crude aromatic urethane is lowered down to about 30% when thermally treated at 180° C. for 1 hour. In contrast thereto, in the case of the process of the invention, the purity of the crude aromatic urethane can be held to a high level of more than 90%. According to the process of the invention, the purity of a crude aromatic urethane obtained from an aromatic nitro compound of an ordinary quality reaches up to 95% and the lowering of the purity after the thermal treatment can be held within a range of several percent.

The process of the invention has further advantages that it is possible to raise the percentage of recovery of the catalyst from the reaction solution even up to 95% and that the degree of corrosion of a reactor material is lowered to below 0.001 mm/yr when using a stainless steel (SUS 316).

DESCRIPTION OF THE PREFERRED EMBODIMENT

The starting aromatic nitro compounds may be mononitro compounds or polynitro compounds including, for example, nitrobenzene, dinitrobenzenes, dinitrotoluenes, nitronaphthalenes, nitroanthracenes, nitrobiphenyls, bis(nitrophenyl)alkanes, bis(nitrophenyl) ethers, bis(nitrophenyl)thioethers, bis(nitrophenyl) sulfons, nitrodiphenoxyalkanes, and heterocyclic compounds such as nitrophenothiazines and 5-nitropyrimidine. Typical of the aromatic nitro compounds are nitrobenzene, o-, m- or p-nitrotoluene, o-nitro-p-xylene, 1-nitronaphthalene, m- or p-dinitrobenzene, 2,4- or 2,6-dinitrotoluene, dinitromesitylene, 4,4'-dinitrobiphenyl, 2,4-dinitrobiphenyl, 4,4'-dinitrodibenzyl, bis(4-nitrophenyl)methane, bis(4-nitrophenyl)ether, bis(2,4-dinitrophenyl)ether, bis(4-nitrophenyl)thioether, bis(4-nitrophenyl)sulfon, bis(4-nitrophenoxy)ethane, $\alpha,\alpha'$-dinitro-p-xylene, $\alpha,\alpha'$-dinitro-m-xylene, 2,4,6-trinitrotoluene, o-, m-, or p-chloronitrobenzene, 1-chloro-2,4-dinitrobenzene, 1-bromo-4-nitrobenzene, 1-fluoro-2,4-dinitrobenzene, o-, m- or p-nitrophenylcarbamate, o-, m- or p-nitroanisole, 2,4-dinitrophenetole, m-nitrobenzaldehyde, p-nitrobenzoyl chloride, ethyl-p-nitrobenzoate, m-nitrobenzenesulfonyl chloride, 3-nitrophthalic anhydride, 3,3'-dimethyl-4,4'-dinitrobiphenyl, 1,5-dinitronaphthalene and the like. These aromatic nitro compounds may be used singly or in combination. Further, isomers and homologues of these compounds may be also employed. Of these, 2,4-dinitrotoluene and 2,6-dinitrotoluene are most preferred since the isocyanates obtained by thermal decomposition of aromatic urethanes prepared from these dinitrotoluenes in accordance with the process of the invention are industrially useful.

The hydroxyl group-containing organic compounds useful in the process of the invention include monohydric alcohols having a primary, secondary or tertiary hydroxyl group, polyhydric alcohols, monohydric phenols and polyhydric phenols. The alcohols include linear or branched alkyl alcohols, cycloalkyl alcohols, alkylene alcohols, cycloalkylene alcohols, aralkyl alcohols and the like, each in the monohydric or polyhydric form. Examples of the alcohols are monohydric alcohols such as methyl alcohol, ethyl alcohol, n- or iso-propyl alcohol, n-, iso- or t-butyl alcohol, linear or branched amyl alcohol, hexyl alcohol, cyclohexyl alcohol, lauryl alcohol, cetyl alcohol, benzyl alcohol, chlorobenzyl alcohol, methoxybenzyl alcohol and the like, dihydric alcohols such as ethylene glycol, diethylene glycol, propylene glycol, dipropylene glycol and the like, trihydric alcohols such as glycerine, hexanetriol and the like, and more functional polyols. Of these, ethyl alcohol is most preferred from the practical point that the aromatic urethane obtained therefrom in accordance with the process of the invention can be thermally decomposed to give an isocyanate.

The phenols useful in the present invention include, for example, phenol, cresol, ethylphenol, linear or branched propylphenol, butyl or higher alkylphenols, catechol, resorcin, 4,4'-dihydroxydiphenylmethane, 2,2'-isopropylidenediphenol, and the like.

The primal catalyst used in the reaction of the invention is a simple substance such as palladium, rhodium or ruthenium, or a catalytically active compound thereof. Examples of the catalytically active compounds are the halides, cyanides, thiocyanides, isocyanides, oxides, sulfates, nitrates and carbonyl compounds of the above metals, and complex salts of the halides and ammonia and the like.

These primal catalysts may be used as such in the urethanation reaction or may be supported on inert carriers such as alumina, silica, carbon, barium sulfate, calcium carbonate, asbestos, bentonite, diatomaceous earth, Fuller's earth, an organic ion-exchange resin, magnesium silicate, aluminum silicate, Molecular Sieves, and the like. In this connection, the carriers may be placed in a reactor independently of the primal catalyst such as palladium, rhodium, ruthenium or compound thereof.

In the present invention, the Lewis acid is employed as a promoter. The Lewis acids useful in the present invention are those described in "Physical Organic Chemistry," 1962, by Jack Hine and published by McGrew Hill Book Co., New York, including Bronsted acids. The Lewis acids are halides, sulfates, acetates, phosphates and nitrates of the metals tin, titanium, germanium, aluminum, iron, copper, nickel, zinc, cobalt, manganese and the like, and include, for example, ferric chloride, ferrous chloride, stannic chloride, stannous chloride, aluminum chloride, cupric chloride, cuprous chloride, copper acetate, and the like. Of these, ferric chloride is preferred.

Ammonia which is one component of the catalytic system useful in the process of the invention may be fed to the reactor separately from the starting materials and the other catalytic components. Alternatively, ammonia may be used by treatment with part of other catalytic components to convert it into a suitable compound such as a complex or an adduct. For example, a palladium chloride-ammonia complex typical of which is $PdCl_2(NH_3)_2$ or $PdCl_2(NH_3)_4$ may be first prepared and then applied to the reaction system though ammonia and palladium chloride may be separately added to the reaction system. It will be noted that the amount of the principal catalytic component such as palladium chloride is sufficient to be smaller than those required in known processes, so that the manner of the addition or application of the catalytic components is not so important.

Preferably, ammonia is used in the form of complexes with ferrous chloride or ferric chloride, e.g., those expressed by formulae $FeCl_2(NH_3)_n$ and $FeCl_3(NH_3)_m$ (in which n and m are independently an integer of 1-10) or complexes with germanium chloride, e.g., those expressed by formulae $GeCl_4(NH_3)_2$ and $GeCl_4(NH_3)_2$. These complexes can be readily prepared without resorting to any specific technique. That is, it is sufficient to agitate catalytic components required to form an intended complex in a suitable solvent such as benzene, monochlorobenzene, dichlorobenzene, ethanol or the like, or to add such catalytic component or components to ammonia under agitation. It should be noted that, in some cases, the preparation in an atmosphere of carbon monoxide results in complexes imparted with stronger activity. If necessary, the solvent or an excess of ammonia employed is removed by distillation.

The amount of ammonia in the reaction system is generally in the range of 0.1-5 moles, preferably 0.2-3 moles, per mole of anions of a Lewis acid. Most preferably, approximately equimolar amounts of ammonia and anions are used. Less amount than 0.1 mole of ammonia per mole of the anions will have a possibility of producing a crude aromatic urethane of high quality but does not generally show a satisfactory effect. On the other hand, larger amount than 5 moles of ammonia is usable but does not offer any particular advantages. As described hereinabove, one of the prominent features of the present invention resides in the use of ammonia as one component of the catalytic system of the invention. As a matter of course, a tertiary amine may be used in combination with ammonia in such an amount as not to counteract the above-described effects of the present invention.

If desired, small amount of water may be added to the reaction system. The addition of water to the reaction system contributes to accelerate the reaction velocity to a considerable extent, making it possible to produce an intended product in high yield within a very short period of time. Though the amount of water varies depending on the type of a starting aromatic nitro compound, the kind and amount of a catalyst, it is generally in the range of 0.01-2 moles, preferably 0.01-1 mole, per mole of a starting nitro compound. Especially when 2,4-nitrotoluene is used as a starting material for the urethanation reaction in the presence of a catalyst composed of palladium chloride and a ferrous chloride-ammonia complex, the amount of water is preferred to be in the range of 0.1-0.6 moles per mole of 2,4-dinitrotoluene.

The presence of water in the reaction system in the above ranges does not give any adverse effect on the reactor with regard to the corrosion of the reactor material. Water may be added to the reaction system by any of known manners. For example, water may be added to starting materials, a solvent or the like to form a solution thereof or a mixture therewith, or may be added in the form of crystal water or a substance capable of producing water on the reaction.

In the reaction of the present invention, the catalytic components are primarily deposited in the form of solids after completion of the reaction due to presence of the ammonia, it thus being possible to separate and collect the solid catalyst from the reaction solution. The structural form of the thus collected catalyst is not presently known, but it has been found that it may be reused as it is or after treatment by a suitable method such as washing with a solvent.

In the process of the invention, although no specific solvent is required to be added to the reaction system since the hydroxyl group-containing organic compound serves as solvent, a solvent may be used. Examples of the solvent include aromatic solvents such as benzene, toluene, xylene, and the like, nitriles such as acetonitrile, benzonitrile and the like, sulfones such as sulfolane and the like, aliphatic halogenated hydrocarbons such as 1,1,2-trichloro-1,2,2-trifluoroethane and the like, halogenated aromatic hydrocarbons such as monochlorobenzene, dichlorobenzene, trichlorobenzene and the like, ketones, esters, tetrahydrofuran, 1,4-dioxane, 1,2-dimethoxyethane, and the like. It is desired that the reaction is effected at least in equimolar or greater ratios of the hydroxyl group-containing organic compound and carbon monoxide to the aromatic nitro compound. Though the amount of the platinum group metal with regard to the aromatic nitro compound may widely vary depending on the kind of the metal and other reaction conditions, the weight ratio to the aromatic nitro compound is generally in the range of $1-1 \times 10^{-5}$, preferably $5 \times 10^{-1}-1 \times 10^{-4}$ when calculated as elemental metal. For example, when the reaction is conducted by a batch process using dinitrotoluene as a starting material, the weight ratio of the platinum group metal to dinitrotoluene as small as $5 \times 10^{-4}-1 \times 10^{-5}$ calculated as elemental metal is sufficient to make the reaction to proceed satisfactorily. In this connection, however, it is preferred that when the reaction is conducted by an industrially advantageous continuous manner, larger amount of the catalyst is used to increase an amount of formation of urethane product per unit time.

The Lewis acid used as a promoter is generally employed in a weight ratio, to the nitro group of an aromatic nitro compound, of $2-2 \times 10^{-3}$, preferably $1-5 \times 10^{-2}$.

Although the manner of charging the starting materials is not particularly limited, it is desirable that all or part of the aromatic nitro compound and the Lewis acid is dissolved in the hydroxyl group-containing organic compound or a suitable solvent and then added to the reaction system. The order of addition of the starting materials also is not limited and may be arbitrarily changed within the limitations of the apparatus used. For instance, a hydroxyl group-containing compound, catalytic components, ammonia, and aromatic nitro compound may be introduced altogether into a suitable pressure-resistant reactor such as an autoclave, into which carbon monoxide is further fed under pressure, followed by heating under agitating conditions until the reaction is complete. Carbon dioxide which is formed during the reaction is exhausted by any suitable means, and the carbon monoxide may be fed either intermittently or continuously. The reaction may be effected by a batchwise, semi-continuous or continuous method under urethanation conditions. The reaction is generally effected under an initial carbon monoxide pressure of 10 kg/cm²-500 kg/cm². The reaction temperature is generally in the range of 80° to 260° C., preferably from 140° to 200° C. The reaction proceeds more rapidly at higher temperatures. When the concentration of aromatic nitro compound is high and is likely to be decomposed during the reaction, the reaction may be carried out by a two-stage process, the first stage reaction being effected in the vicinity of 160° C. and the second stage reaction in the vicinity of 190° C.

The reaction time varies depending upon the property of the nitro compound, reaction temperature and pressure, kind and amount of catalyst, and kind and type of reaction apparatus and it is generally in the range of 5 minutes to 6 hours.

After completion of the reaction, the reaction mixture is cooled and the gases in the reactor are evacuated therefrom. Then, the thus cooled reaction mixture is subjected to filtration, distillation or other suitable separation treatments for separating the produced urethane from unreacted materials, byproducts, solvent and catalyst.

As will be understood from the foregoing detailed description, the process of the invention can more easily produce crude aromatic urethanes having excellent thermal stability than processes using known catalytic systems composed of platinum group metals, Lewis acids and tertiary amines. In addition, crude aromatic urethanes obtained according to the process of the invention are so high in quality that the urethanes can be directly thermally decomposed into corresponding isocyanates without being purified by any specific techniques. This is believed due to a fact that the crude aromatic urethanes which have been obtained by removing most of the catalyst from the reaction solution by filtration and concentrating the resulting filtrate are contaminated with only small amounts of the catalytic components including a Lewis acid such as $FeCl_2$, $NH_3$, a platinum group metal compound such as $PdCl_2$ and a tertiary amine which will be often found in a urethane product obtained by prior art processes. Moreover, the crude aromatic urethane obtained according to the present invention scarecely contains an unreacted aromatic nitro compound since the catalytic system employed is very high in activity, thus leading to the high quality of the urethane product. The above fact that the aromatic urethane can be produced without being contaminated with the unreacted aromatic nitro compound is very advantageous in that the danger of explosion can be avoided when the aromatic urethane is subsequently converted into a corresponding isocyanate by thermal decomposition.

500 ml autoclave for reaction at temperatures of 160°–170° C. under an initial carbon monoxide pressure of 100 kg/cm$^2$ for different periods of time indicated in the Table. The FeCl$_2$–NH$_3$ complex used was prepared as follows. 36 g of ferrous chloride was suspended in 300 ml of ethanol, into which was blown about 10 g of ammonia gas while agitating. The suspension was filtered and the resulting cake was washed with a small amount of ethanol to obtain 45 g of a ferrous chloride-ammonia complex.

Table 1

| Classification | | Catalyst | | | reaction time (min) | Crude urethane | | | | | net yield of urethane (%) | purity after heating (wt %) | Corrosion rate (mm/yr) |
|---|---|---|---|---|---|---|---|---|---|---|---|---|---|
| | PdCl$_2$ (g) | FeCl$_2$ (g) | NH$_3$ (g) | FeCl$_2$-NH$_3$ complex (g) | | yield (g) | nitro benzene (%) | urethane (%) | aniline (%) | others[a] (%) | | | |
| Example 1 | 0.1 | 12.7 | 3.4 | 0 | 30 | 16.0 | 0 | 95 | 3 | 2 | 92 | 92 | 0.01 |
| " 2 | " | 16.6[c] | " | 0 | 40 | 16.0 | 0 | 93 | 5 | 2 | 90 | 88 | 0.02 |
| " 3 | " | 0 | 0 | 16.1 | 30 | 16.3 | 0 | 96 | 2 | 2 | 95 | 93 | <0.001 |
| Reference 1 | " | 12.7 | 0 | 0 | 60[d] | 15.8 | 5 | 78 | 7 | 10 | 75 | 50 | 1.50 |
| 2 | " | 0 | 3.4 | 0 | 60[e] | 14.0 | 90 | <1 | 2 | 18 | <1 | — | <0.001 |
| 3 | 0 | 0 | 0 | 16.1 | 60[e] | 13.0 | 50 | 0 | 10 | 40 | 0 | — | <0.001 |
| 4 | 0.1 | 0 | 30[b] | 0 | 60[e] | 14.0 | 90 | <1 | 2 | 18 | <1 | — | <0.001 |
| 5 | " | 12.7 | 16[b] | 0 | 30 | 17.0 | 0 | 94 | 3 | 3 | 97 | 70 | 0.01 |

Note
[a]Tarry matter.
[b]Determined according to the afore-described thermal stability test.
[c]FeCl$_3$.
[d]Slight pressure drop was observed.
[e]Pressure drop was hardly observed.

The aromatic urethanes obtained have numerous uses as starting materials for preparing agricultural chemicals, isocyanates and polyurethanes.

The present invention will be particularly illustrated by way of the following examples, which should not be construed as limiting thereto the present invention. In these examples, all the reactions were conducted in a stainless steel (SUS 316), electromagnetically agitated autoclave. The degree of corrosion of a metal material was calculated from the weight reduction and surface area of an agitating blade (made of SUS 316). The yield indicated in the Examples was calculated on the basis of results of gas-chromatographic and liquid-chromatographic analyses. The thermal stability test was conducted as follows. The reaction solution was filtered at a normal temperature to remove a catalyst therefrom. The resulting filtrate was dried up or thermally treated to obtain a crude aromatic urethane. 1 g of the urethane was placed in a test tube and heated at 180° C. for 1 hour in an atmosphere of nitrogen. After cooling, alcohol was added to the test tube to dissolve the urethane therein. The solution was subjected to gas-chromatographic and liquid-chromatographic analyses from which the purity of the urethane was determined. The purity was compared with that which had been previously determined prior to the heating in a manner similar to the above-described procedure.

EXAMPLES 1–3

12.3 g of nitrobenzene, 150 ml of ethyl alcohol and a catalytic system indicated in Table 1 were placed in a After completion of the reaction of Example 1, the reaction solution was cooled down to room temperature. Then, the nitrogen gas was purged from the autoclave and the reaction solution was withdrawn from the autoclave to remove insoluble matters therefrom by filtration. 16.0 g of the solid matter was obtained. The solid matter was analyzed by an atomic absorption method, revealing that 95% of palladium fed to the reactor was recovered.

The excellency of the process using the catalytic systems of the specific type according to the present invention will be understood by comparison with known processes, e.g., a process of Reference 4 using a palladium catalyst and a tertiary amine (such as disclosed in U.S. Pat. No. 3,993,685), a process of Reference 1 using a palladium catalyst and a Lewis acid (such as disclosed in U.S. Pat. No. 3,531,512) and a process of Reference 5 using a palladium catalyst, a Lewis acid and a tertiary amine.

EXAMPLE 4–10

In these examples, different kinds of aromatic nitro compounds indicated in Table 2 were used. 150 ml of ethyl alcohol, 0.1 g of PdCl$_2$, 16.1 g of FeCl$_2$-NH$_3$ complex were placed in an autoclave together with each of the aromatic nitro compounds for reaction at temperatures of 160°–170° C. under an initial pressure of carbon monoxide of 100 kg/cm$^2$G for different periods of time indicated in the Table 2. The crude urethanes obtained by a series of the experiments were found to contain no unreacted nitro compounds, respectively.

Table 2

| Classification | nitro compound | | Reaction time (min) | Crude urethane | | | | Net yield of urethane (%) | purity[b] after heating (%) | corrosion rate (mm/yr) |
|---|---|---|---|---|---|---|---|---|---|---|
| | kind | amount (g) | | yield (g) | urethane (%) | amines (%) | others[a] (%) | | | |
| Example 4 | p-nitrotoluene | 13.7 | 100 | 17.8 | 95 | 3 | 2 | 94 | 91 | 0.001 |
| Example 5 | o-chloronitrobenzene | 15.8 | 120 | 20.0 | 93 | 3 | 4 | 93 | 88 | 0.002 |
| Example 6 | 3,4-dichloronitrobenzene | 19.2 | 120 | 23.2 | 94 | 3 | 3 | 93 | 90 | 0.002 |
| Example 7 | 2,4-dinitrotoluene | 27.3 | 210 | 39.8 | 91 | 5 | 4 | 91 | 86 | 0.001 |
| Example 8 | 2,6-dinitrotoluene | " | " | 39.8 | 92 | 4 | 4 | 92 | 88 | 0.001 |

Table 2-continued

| Classification | nitro compound kind | amount (g) | Reaction time (min) | Crude urethane yield (g) | urethane (%) | amines (%) | others[a] (%) | Net yield of urethane (%) | purity[b] after heating (%) | corrosion rate (mm/yr) |
|---|---|---|---|---|---|---|---|---|---|---|
| Example 9 | crude dinitrotoluene[c] | " | 200 | 40.5 | 90 | 5 | 5 | 91[d] | 85 | 0.005 |
| Example 10[e] | " | " | 230 | 40.5 | 86 | 8 | 6 | 87[d] | 81 | 0.010 |
| Reference 6[f] | " | " | 240 | 39.7 | 91 | 4 | 5 | 91 | 50 | 0.010 |

Note
[a] and [b] see Table 1.
[c] Commercial crude DNT containing 2,4-isomer 76%, 2,6-isomer 19%, ortho isomer 4%.
[d] Ratio of 2,4-isomer and 2,6-isomer contained in crude dinitrotoluene.
[e] Instead of using 16.1 g of $FeCl_2$-$NH_3$ complex, 12.7 g of $FeCl_2$ and 3.4 g of $NH_3$ were employed.
[f] Instead of using 16.1 g of $FeCl_2$-$NH_3$ complex, 12.7 g of $FeCl_2$ and 16.0 g of pyridine were employed.

EXAMPLES 11–13

In these examples, water was added to a reaction system to show its effect. That is, Example 1 was repeated using 27.3 g of 2,4-dinitrotoluene, 150 ml of ethyl alcohol and 15 g of $FeCl_2$-$NH_3$ complex together with water, with the results shown in Table 3 below.

The purities of the crude urethanes obtained by these experiments were found to be in the range of 90-93% and, after heat treatment, were slightly lowered to 87-90%.

EXAMPLES 14–19

In these examples, different types of monohydric alcohols indicated in Table 4 were used as hydroxyl group-containing organic compound. 12.3 g of nitrobenzene, 150 ml of the alcohol indicated in Table 4, 0.02 g of $PdCl_2$, 15.0 g of $FeCl_2$-$NH_3$ complex and 0.8 g of water were placed in an autoclave for reaction at temperatures of 160°–170° C. under an initial pressure of carbon monoxide of 100 kg/cm²G for different periods of reaction time indicated in the Table 4.

EXAMPLE 20–21

In these examples, $RhCl_2$ and $RuCl_2$ were used instead of $PdCl_2$. That is, 27.3 g of 2,4-dinitrotoluene, 150 ml of isobutyl alcohol, 0.05 g of the primal catalyst indicated in Table 5, 20 g of $FeCl_3$-$NH_3$ complex and 1.2 g of water were placed in an autoclave for reaction at temperatures of 160°–170° C. under an initial pressure of carbon monoxide of 100 kg/cm²G for different periods of reaction time with the results shown in the Table 5.

Table 5

| Example No. | Main catalyst | Reaction time (min) | Net yield of urethane (%) |
|---|---|---|---|
| 3 | $PdCl_2$ | 90 | 90 |
| 20 | $RhCl_2$ | 120 | 80 |
| 21 | $RuCl_2$ | 150 | 75 |

What is claimed is:

1. A process for producing an aromatic urethane by reacting an aromatic nitro compound, a hydroxyl group-containing organic compound selected from the group consisting of monohydric alcohols, polyhydric alcohols, monohydric phenols and polyhydric phenols, characterized in that the reaction is conducted in the presence of a catalytic system composed of (1) a member selected from the group consisting of palladium, ruthenium and rhodium and halides, cyanides, thiocyanides, isocyanides, oxides, sulfates, nitrates and carbonyl compounds thereof, (2) a Lewis acid, and (3) ammonia under an initial pressure of carbon monoxide of 10–500 kg/cm² and at a temperature of 80°–260° C.

2. A process according to claim 1, wherein said Lewis acid and said ammonia are admixed to form a complex thereof and then added to the reaction system.

3. A process according to claim 1, wherein the amount of said ammonia in the reaction system is in the range of 0.1–5 moles per mole of the anions of said Lewis acid.

4. A process according to claim 1, wherein water is added to the reaction system.

Table 3

| Example No. | water (g) | $PdCl_2$ (g) | reaction temperature (° C) | reaction time (min) | net yield of urethane (%) | corrosion rate (mm/yr) |
|---|---|---|---|---|---|---|
| 7 | 0 | 0.1 | 160 – 170 | 210 | 91 | 0.001 |
| 11 | 1.2 | " | 160 – 220[a] | 10 | 80 | 0.005 |
| 12 | " | 0.01 | 170 – 180 | 180 | 91 | 0.001 |
| 13 | 2.4 | " | " | 100 | 89 | 0.01 |

Note:
[a] Because of the considerable generation of heat, the temperature of the system was hard to control and was raised up to 220° C.

Table 4

| Example No. | Alcohol | Reaction time (min) | Crude urethane yield (g) | urethane (%) | amine (%) | others[a] (%) | Net yield of urethane (%) | Purity after[b] heating (%) | Corrosion rate (mm/yr) |
|---|---|---|---|---|---|---|---|---|---|
| 14 | methyl | 120 | 14.5 | 94 | 4 | 2 | 90 | 91 | 0.005 |
| 15 | ethyl | 90 | 16.0 | 93 | 4 | 3 | 93 | 90 | 0.010 |
| 16 | n-propyl | 100 | 17.0 | 96 | 3 | 3 | 91 | 91 | 0.010 |
| 17 | iso-propyl | 150 | 17.0 | 95 | 3 | 2 | 90 | 89 | 0.005 |
| 18 | n-butyl | 150 | 19.0 | 91 | 5 | 4 | 90 | 85 | 0.005 |
| 19 | iso-butyl | 160 | 19.0 | 95 | 3 | 2 | 91 | 89 | 0.001 | note [a] and [b]: see Table 1.

5. A process according to claim 4, wherein the amount of said water is in the range of 0.01–2 moles per mole of the aromatic nitro compound.

6. A process according to claim 1, wherein said aromatic nitro compound is a member selected from the group consisting of nitrobenzene, nitrotoluene, dinitrobenzene and dinitrotoluene.

7. A process according to claim 1, wherein said monohydric alcohol is a member selected from the group consisting of methyl alcohol, ethyl alcohol, n- and iso-propyl alcohol, and n-, iso- and t-butyl alcohol.

8. A process according to claim 1, wherein said Lewis acid is a member selected from the group consisting of ferric chloride and ferrous chloride.

* * * * *